United States Patent [19]

Klemm

[11] Plant 5,206

[45] Mar. 13, 1984

[54] CARNATION NAMED KLERONSTAR

[76] Inventor: Siegfried Klemm, Hanfacker 9, 7000 Stuttgart 50, Fed. Rep. of Germany

[21] Appl. No.: 401,963

[22] Filed: Jul. 26, 1982

[51] Int. Cl.[3] ..... A01H 5/00

[52] U.S. Cl. ..... Plt./70

[58] Field of Search ..... Plt./70

*Primary Examiner*—James R. Feyrer

*Attorney, Agent, or Firm*—Chas. W. Rummler

[57] ABSTRACT

A new carnation cultivar distinguished by its bright generally orange colored blooms of medium size, which are borne on sturdy pedicels carried by long, strong peduncles, and by its continuous and abundant production of flowers.

1 Drawing Figure

BACKGROUND OF THE NEW PLANT

This new carnation cultivar originated as a sport of the unpatented cultivar named "Ministar", this sport having been discovered by me on Feb. 1, 1974, in a field of the variety "Ministar" growing in my greenhouse at Stuttgart, West Germany. The extraordinary bright orange coloring of this flower appeared that it could have substantial commercial merit and this led me to propagate this flower by cuttings from the parent plant which were rooted in my greenhouse at Stuttgart and grown to flowering maturity. Successive generations of this new cultivar propagated by means of cuttings have demonstrated that the novel characteristics of the first asexual reproduction of this sport hold true from generation to generation and appear to be firmly fixed.

DESCRIPTION OF THE DRAWING

My new carnation variety is illustrated by the accompanying full color photographic drawing, which shows the inflorescence of a fully grown plant, the view including buds in various stages of opening, as well as fully opened flowers, the color rendition being as nearly true as it is reasonably possible to obtain by means of conventional photographic procedures.

DESCRIPTION OF THE NEW PLANT

The following is a detailed description of my new carnation cultivar based upon observation of plants growing under conventional greenhouse procedures, the color designations being according to The H.C.C. Colour Chart of Robert F. Wilson issued by The British Colour Council in collaboration with The Royal Horticultural Society of London, England.

THE PLANT

Origin: Sport.

Parentage: The cultivar named "Ministar" (unpatented).

Clssification:

*Botanic.*—*Dianthus caryophyllus.*

*Commercial.*—Spray carnation.

Form: Bush.

Height: From about 90 cm. to about 120 cm.

Growth: Vigorous and upright with moderate strength.

Branching: Normal.

Foliage: Quantity — Moderate.

*Leaf size.*—Moderate.

*Leaf shape.*—Oblong with entire margins.

*Texture.*—Smooth. *Color.*—Upper side — Blue-Green. Under side — Blue-Green.

THE BUD

Size: Medium, about 15 mm. in diameter and about 38 mm. long.

Form: Generally ovate, becoming cylindrical when beginning to open.

Opening rate: Moderate.

Color:

*When sepals first divide.*—Yellow-Green.

*When petals begin to unfurl.*—Yellow-Green.

Sepals:

*Condition.*—Upstanding.

*Color.*—Inside — Grey-Green. Outside — Yellow-Green.

Calyx:

*Shape.*—Cylindrical.

*Size.*—Moderate, about 16 mm. broad and about 18 mm. long.

*Splitting.*—The calyx does not split.

*Aspect.*—Smooth.

Peduncle: Rigid and erect.

*Color.*—Grey-Green.

THE FLOWER

Blooming habit: Continuous and profuse.

Size of bloom: Medium.

*Diameter.*—About 50 to about 55 mm.

*Depth.*—About 25 mm.

Borne: Singly on strong, upright stems.

Shape: High center when bloom opens; this form does not change as the flower matures.

Petalage: Number of petals — About 32.

*Arrangement.*—Generally imbricated.

*Shape.*—Fan-shaped with serrated margins.

*Color.*—Outer petals — HCC 612/1. Inside petals — HCC 614/1 with some petals having very few red strips about 3 to 5 mm. long extending longitudinally from the serrated petal tips. The petal also has a very small and fine red band around the petal body. Reverse side — HCC 614/1.

*Texture.*—Soft.

*Appearance.*—Shiny.

Peduncle: Sturdy and upright.

*Length.*—About 42 cm.

*Color.*—Grey-Green.

Persistence: The flowers hang on and dry.

Fragrance: Very weak.
Lasting quality:
*On plant.*—About 16 days.
*As a cut flower.*—About 12 days.

REPRODUCTIVE ORGANS

Stamens: Anthers and pollen are rarely present.
Pistils: About 3 in number.
*Length.*—About 35 mm.
*Stigmas.*—Color — Cream Yellow.
Fruit: Fertile.
*Shape.*—Cylindrical.

*Color.*—Green/Brown at maturity.

I claim:

1. A new and distinct carnation cultivar, substantially as herein shown and described, characterized by its high productivity of bright orange colored flowers having fan-shaped petals with few short red stripes extending longitudinally inward from the petal tips, the flowers being borne singly on rigid and erect pedicels carried in spray arrangement on a sturdy, upright peduncle.

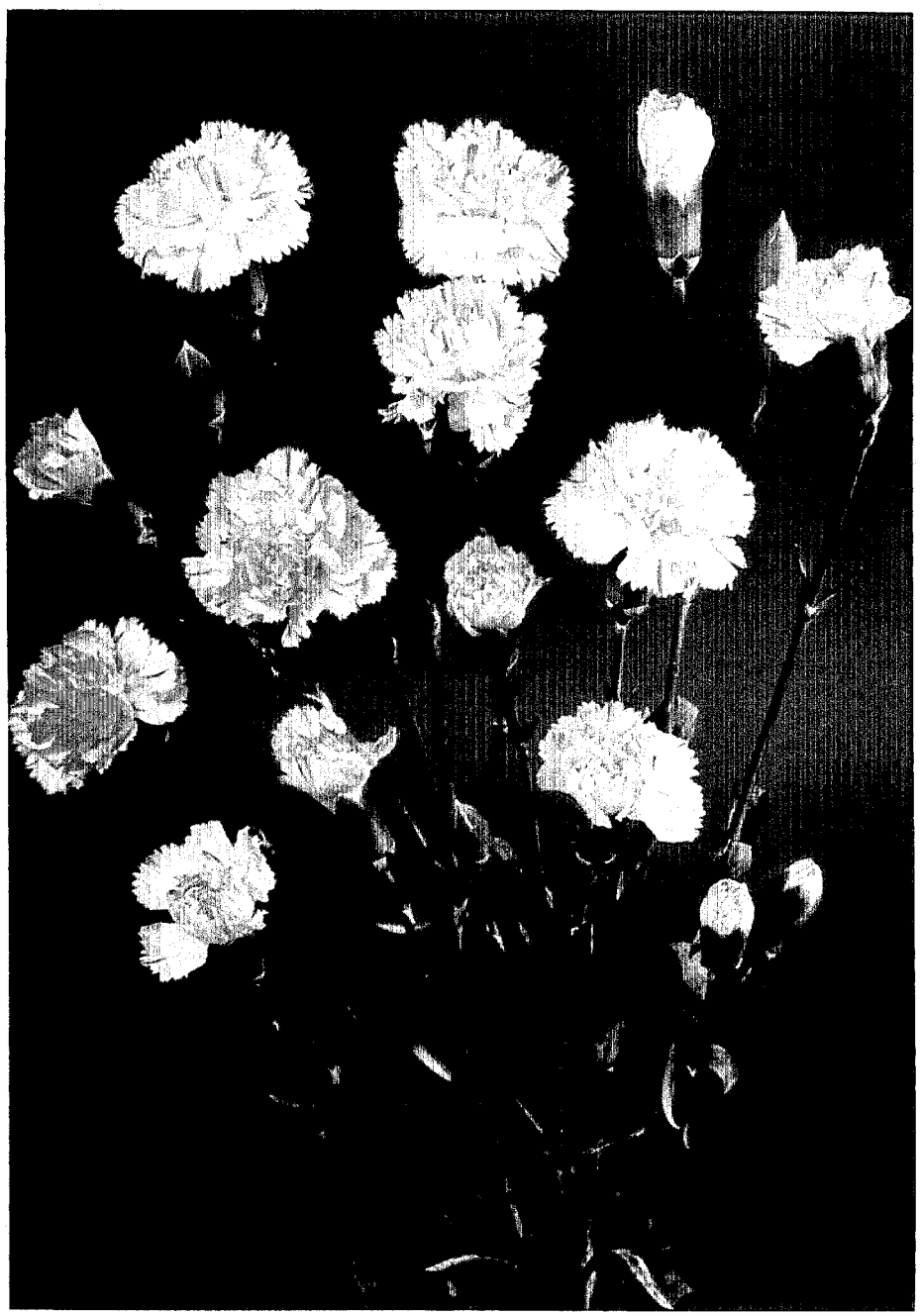

* * * * *